(12) United States Patent
Kittler, Jr. et al.

(10) Patent No.: US 7,550,197 B2
(45) Date of Patent: *Jun. 23, 2009

(54) NON-TOXIC FLAKES FOR AUTHENTICATION OF PHARMACEUTICAL ARTICLES

(75) Inventors: Wilfred C. Kittler, Jr., Rohnert Park, CA (US); Alberto Argoitia, Santa Rosa, CA (US); Paul G. Coombs, Santa Rosa, CA (US); Charles T. Markantes, Santa Rosa, CA (US)

(73) Assignee: JDS Uniphase Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/776,025

(22) Filed: Jul. 11, 2007

(65) Prior Publication Data

US 2008/0019924 A1 Jan. 24, 2008

Related U.S. Application Data

(63) Continuation-in-part of application No. 10/641,695, filed on Aug. 14, 2003, now Pat. No. 7,258,915.

(60) Provisional application No. 60/807,097, filed on Jul. 12, 2006.

(51) Int. Cl.
 *B32B 5/16* (2006.01)
(52) U.S. Cl. ................... 428/323; 428/328; 428/403; 428/407
(58) Field of Classification Search ............. 428/323, 428/328, 403, 407
See application file for complete search history.

(56) References Cited

U.S. PATENT DOCUMENTS

| | | | |
|---|---|---|---|
| 2,570,856 A | 10/1951 | Pratt et al. ................. 41/32 |
| 3,011,383 A | 12/1961 | Sylvester et al. ............ 359/584 |
| 3,123,490 A | 3/1964 | Bolomey et al. ............ 106/291 |
| 3,338,730 A | 8/1967 | Slade et al. ................ 428/142 |
| 3,610,721 A | 10/1971 | Abramson et al. .......... 350/3.5 |
| 3,627,580 A | 12/1971 | Krall ........................ 117/238 |
| 3,633,720 A | 1/1972 | Tyler ........................ 400/105 |
| 3,676,273 A | 7/1972 | Graves ........................ 161/3 |
| 3,790,407 A | 2/1974 | Merten et al. .............. 117/240 |
| 3,791,864 A | 2/1974 | Steingroever ............... 117/238 |
| 3,845,499 A | 10/1974 | Ballinger ................... 346/74.3 |
| 3,853,676 A | 12/1974 | Graves ........................ 161/5 |
| 3,873,975 A | 3/1975 | Miklos et al. .............. 360/25 |
| 4,011,009 A | 3/1977 | Lama et al. ................ 359/571 |
| 4,053,433 A | 10/1977 | Lee ......................... 252/408 |
| 4,054,922 A | 10/1977 | Fichter ..................... 346/74.3 |
| 4,066,280 A | 1/1978 | LaCapria ................... 283/91 |
| 4,099,838 A | 7/1978 | Cook et al. ................. 359/537 |
| 4,126,373 A | 11/1978 | Moraw ........................ 359/2 |
| 4,155,627 A | 5/1979 | Gale et al. ................. 359/568 |
| 4,168,983 A | 9/1979 | Vittands et al. ........... 106/14.12 |
| 4,197,563 A | 4/1980 | Michaud .................... 346/74.3 |
| 4,244,998 A | 1/1981 | Smith ....................... 428/195 |
| 4,271,782 A | 6/1981 | Bate et al. .................. 118/623 |
| 4,310,584 A | 1/1982 | Cooper et al. ............... 428/212 |
| 4,398,798 A | 8/1983 | Krawczak et al. ........... 359/573 |
| 4,434,010 A | 2/1984 | Ash ......................... 106/415 |
| 4,543,370 A | 9/1985 | Porter et al. ................ 523/100 |
| 4,543,551 A | 9/1985 | Peterson .................... 335/284 |
| 4,705,300 A | 11/1987 | Berning et al. ............... 283/91 |
| 4,705,356 A | 11/1987 | Berning et al. ............. 350/166 |
| 4,721,217 A | 1/1988 | Phillips et al. ............. 215/230 |
| 4,756,771 A | 7/1988 | Brodalla et al. ............ 148/244 |
| 4,779,898 A | 10/1988 | Berning et al. .............. 283/58 |
| 4,788,116 A | 11/1988 | Hochberg .................... 430/21 |
| 4,838,648 A | 6/1989 | Phillips et al. ............. 359/585 |
| 4,867,793 A | 9/1989 | Franz et al. ................ 106/415 |
| 4,930,866 A | 6/1990 | Berning et al. ............. 359/589 |
| 4,931,309 A | 6/1990 | Komatsu et al. ............ 427/599 |
| 5,002,312 A | 3/1991 | Phillips et al. .............. 283/72 |
| 5,009,486 A | 4/1991 | Dobrowolski et al. ....... 359/580 |
| 5,059,245 A | 10/1991 | Phillips et al. ........... 106/31.65 |
| 5,079,058 A | 1/1992 | Tomiyama ................... 428/40 |

(Continued)

FOREIGN PATENT DOCUMENTS

AU 488652 11/1977

(Continued)

OTHER PUBLICATIONS

R. Domnick et al, "Influence of Nanosized Metal Clusters on the Generation of Strong Colors and Controlling of their Properties through Physical Vapor Deposition (PVD)" 49th Annual Technical Conference Proceedings (2006), Society of vacuum Coasters.

(Continued)

*Primary Examiner*—Leszek Kiliman
(74) *Attorney, Agent, or Firm*—Allen, Dyer, Doppelt, Milbrath & Gilchrist, P.A.

(57) ABSTRACT

In one embodiment of the present invention, non-toxic inorganic flakes are used for identification and anticounterfeit protection of pharmaceutical articles, such as pills, tablets and capsules, having a core of a biologically active material and/or a biologically inert material. Non-toxic inorganic authentication flakes, either optically variable flakes or taggant flakes having one or more symbols and/or a selected shape are disposed on the surface or inside of the pharmaceutical article.

20 Claims, 3 Drawing Sheets

U.S. PATENT DOCUMENTS

| | | | |
|---|---|---|---|
| 5,079,085 A | 1/1992 | Hashimoto et al. | 428/327 |
| 5,084,351 A | 1/1992 | Phillips et al. | 428/411.1 |
| 5,106,125 A | 4/1992 | Antes | 283/91 |
| 5,128,779 A | 7/1992 | Mallik | 359/2 |
| 5,135,812 A | 8/1992 | Phillips et al. | 428/403 |
| 5,142,383 A | 8/1992 | Mallik | 359/2 |
| 5,171,363 A | 12/1992 | Phillips et al. | 106/31.65 |
| 5,177,344 A | 1/1993 | Pease | 235/449 |
| 5,186,787 A | 2/1993 | Phillips et al. | 216/36 |
| 5,192,611 A | 3/1993 | Tomiyama et al. | 428/354 |
| 5,214,530 A | 5/1993 | Coombs et al. | 359/359 |
| 5,223,360 A | 6/1993 | Prengel et al. | 430/39 |
| 5,254,390 A | 10/1993 | Lu | 428/156 |
| 5,278,590 A | 1/1994 | Phillips et al. | 359/589 |
| 5,279,657 A | 1/1994 | Phillips et al. | 106/31.65 |
| 5,339,737 A | 8/1994 | Lewis et al. | 101/454 |
| 5,364,467 A | 11/1994 | Schmid et al. | 106/404 |
| 5,364,689 A | 11/1994 | Kashiwagi et al. | 428/195.1 |
| 5,368,898 A | 11/1994 | Akedo | 427/510 |
| 5,411,296 A | 5/1995 | Mallik | 283/86 |
| 5,424,119 A | 6/1995 | Phillips et al. | 428/328 |
| 5,437,931 A | 8/1995 | Tsai et al. | 428/446 |
| 5,447,335 A | 9/1995 | Haslop | 283/91 |
| 5,464,710 A | 11/1995 | Yang | 430/1 |
| 5,474,814 A | 12/1995 | Komatsu et al. | 427/549 |
| 5,549,774 A | 8/1996 | Miekka et al. | 156/209 |
| 5,549,953 A | 8/1996 | Li | 428/64.1 |
| 5,571,624 A | 11/1996 | Phillips et al. | 428/403 |
| 5,591,527 A | 1/1997 | Lu | 428/411.1 |
| 5,613,022 A | 3/1997 | Odhner et al. | 385/37 |
| 5,624,076 A | 4/1997 | Miekka et al. | 241/3 |
| RE35,512 E | 5/1997 | Nowak et al. | 101/454 |
| 5,627,663 A | 5/1997 | Horan et al. | 359/2 |
| 5,629,068 A | 5/1997 | Miekka et al. | 428/148 |
| 5,630,877 A | 5/1997 | Kashiwagi et al. | 118/623 |
| 5,648,165 A | 7/1997 | Phillips et al. | 428/346 |
| 5,650,248 A | 7/1997 | Miekka et al. | 430/1 |
| 5,672,410 A | 9/1997 | Miekka et al. | 428/148 |
| 5,700,550 A | 12/1997 | Uyama et al. | 428/212 |
| 5,742,411 A | 4/1998 | Walters | 359/2 |
| 5,744,223 A | 4/1998 | Abersfelder et al. | 428/206 |
| 5,763,086 A | 6/1998 | Schmid et al. | 428/404 |
| 5,811,775 A | 9/1998 | Lee | 235/457 |
| 5,815,292 A | 9/1998 | Walters | 359/2 |
| 5,856,048 A | 1/1999 | Tahara et al. | 430/1 |
| 5,858,078 A | 1/1999 | Andes et al. | 106/437 |
| 5,907,436 A | 5/1999 | Perry et al. | 359/576 |
| 5,912,767 A | 6/1999 | Lee | 359/567 |
| 5,989,626 A | 11/1999 | Coombs et al. | 427/162 |
| 5,991,078 A | 11/1999 | Yoshitake et al. | 359/567 |
| 6,013,370 A | 1/2000 | Coulter et al. | 428/403 |
| 6,031,457 A | 2/2000 | Bonkowski et al. | 340/572.1 |
| 6,033,782 A | 3/2000 | Hubbard et al. | 428/407 |
| 6,043,936 A | 3/2000 | Large | 359/2 |
| 6,045,230 A | 4/2000 | Dreyer et al. | 359/529 |
| 6,068,691 A | 5/2000 | Miekka et al. | 106/403 |
| 6,103,361 A | 8/2000 | Batzar et al. | 428/323 |
| 6,112,388 A | 9/2000 | Kimoto et al. | 29/17.3 |
| 6,114,018 A | 9/2000 | Phillips et al. | 428/200 |
| 6,150,022 A | 11/2000 | Coulter et al. | 428/403 |
| 6,157,489 A | 12/2000 | Bradley, Jr. et al. | 359/584 |
| 6,168,100 B1 | 1/2001 | Kato et al. | 241/1 |
| 6,241,858 B1 | 6/2001 | Phillips et al. | 204/192.15 |
| 6,242,510 B1 | 6/2001 | Killey | 523/204 |
| 6,243,204 B1 | 6/2001 | Bradley, Jr. et al. | 359/585 |
| 6,376,018 B1 | 4/2002 | Kittler | 427/294 |
| 6,403,169 B1 | 6/2002 | Hardwick et al. | 427/548 |
| 6,549,131 B1 | 4/2003 | Cote et al. | 340/572.1 |
| 6,586,098 B1 | 7/2003 | Coulter et al. | 428/403 |
| 6,589,331 B2 | 7/2003 | Ostertag et al. | 106/460 |
| 6,643,001 B1 | 11/2003 | Faris | 356/37 |
| 6,649,256 B1 | 11/2003 | Buczek et al. | 428/323 |
| 6,686,027 B1 | 2/2004 | Caporaletti et al. | 428/195.1 |
| 6,692,031 B2 | 2/2004 | McGrew | 283/93 |
| 6,692,830 B2 | 2/2004 | Argoitia et al. | 428/403 |
| 6,712,399 B1 | 3/2004 | Drinkwater et al. | 283/111 |
| 6,749,777 B2 | 6/2004 | Argoitia et al. | 252/582 |
| 6,749,936 B2 | 6/2004 | Argoitia et al. | 428/402 |
| 6,751,022 B2 | 6/2004 | Phillips | 359/577 |
| 6,759,097 B2 | 7/2004 | Phillips et al. | 427/510 |
| 6,761,959 B1 | 7/2004 | Bonkowski et al. | 428/156 |
| 6,815,065 B2 * | 11/2004 | Argoitia et al. | 428/403 |
| 6,818,299 B2 | 11/2004 | Phillips et al. | 428/403 |
| 6,838,166 B2 | 1/2005 | Phillips et al. | 428/323 |
| 6,902,807 B1 | 6/2005 | Argoitia et al. | 428/403 |
| 6,932,861 B2 | 8/2005 | Augello | 106/205.01 |
| 6,987,590 B2 | 1/2006 | Phillips et al. | 359/2 |
| 7,029,525 B1 | 4/2006 | Mehta | 106/31.6 |
| 7,258,915 B2 * | 8/2007 | Argoitia et al. | 428/323 |
| 2002/0182383 A1 | 12/2002 | Phillips et al. | 428/199 |
| 2003/0058491 A1 | 3/2003 | Holmes et al. | 359/2 |
| 2003/0087070 A1 | 5/2003 | Souparis | 283/91 |
| 2003/0190473 A1 | 10/2003 | Argoitia et al. | 428/323 |
| 2004/0009309 A1 | 1/2004 | Raksha et al. | 427/598 |
| 2004/0051297 A1 | 3/2004 | Raksha et al. | 101/489 |
| 2004/0081807 A1 | 4/2004 | Bonkowski et al. | 428/195.1 |
| 2004/0094850 A1 | 5/2004 | Bonkowski et al. | 264/1.34 |
| 2004/0100707 A1 | 5/2004 | Kay et al. | 359/883 |
| 2004/0101676 A1 | 5/2004 | Phillips et al. | 428/323 |
| 2004/0105963 A1 | 6/2004 | Bonkowski et al. | 428/195.1 |
| 2004/0151827 A1 | 8/2004 | Argoitia et al. | 427/7 |
| 2005/0037192 A1 | 2/2005 | Argoitia et al. | 428/323 |
| 2005/0063067 A1 | 3/2005 | Phillips et al. | 359/623 |
| 2005/0106367 A1 | 5/2005 | Raksha et al. | 428/195.1 |
| 2005/0123755 A1 | 6/2005 | Argoitia et al. | 428/402 |
| 2005/0128543 A1 | 6/2005 | Phillips et al. | 359/15 |
| 2005/0189060 A1 | 9/2005 | Huang et al. | 156/99 |
| 2006/0035080 A1 | 2/2006 | Argoitia | 428/402 |
| 2006/0077496 A1 | 4/2006 | Argoitia | 359/2 |
| 2007/0058227 A1 | 3/2007 | Raksha et al. | 359/2 |
| 2007/0077218 A1 | 4/2007 | Weinling et al. | 424/63 |
| 2008/0069979 A1 | 3/2008 | Raksha et al. | 428/29 |

FOREIGN PATENT DOCUMENTS

| | | |
|---|---|---|
| DE | 1696245 | 1/1972 |
| DE | 3932505 | 4/1991 |
| DE | 4212290 | 5/1993 |
| DE | 4343387 | 6/1995 |
| DE | 19611383 | 9/1997 |
| DE | 19731968 | 1/1999 |
| DE | 19744953 | 4/1999 |
| DE | 19639165 | 10/2003 |
| EP | 0138194 | 10/1984 |
| EP | 0185396 | 12/1985 |
| EP | 0341002 | 11/1989 |
| EP | 0420261 | 4/1991 |
| EP | 0453131 | 10/1991 |
| EP | 0556449 | 8/1993 |
| EP | 406667 | 1/1995 |
| EP | 0660262 | 1/1995 |
| EP | 0170439 | 4/1995 |
| EP | 710508 | 5/1996 |
| EP | 0756945 | 2/1997 |
| EP | 0395410 | 8/1997 |
| EP | 0698256 | 10/1997 |
| EP | 0741370 | 5/1998 |
| EP | 0914261 | 5/1999 |
| EP | 0953937 | 11/1999 |
| EP | 1174278 | 1/2002 |
| EP | 0978373 | 2/2002 |
| EP | 1239307 | 9/2002 |
| EP | 1 353 197 | 10/2003 |
| EP | 1498545 | 1/2005 |

| | | |
|---|---|---|
| EP | 1516957 | 3/2005 |
| EP | 1529653 | 5/2005 |
| EP | 1674282 | 6/2006 |
| EP | 1719636 | 11/2006 |
| EP | 1 741 757 | 1/2007 |
| EP | 1745940 | 1/2007 |
| EP | 1760118 | 3/2007 |
| GB | 1107395 | 3/1968 |
| GB | 1131038 | 10/1968 |
| JP | 63172279 | 7/1988 |
| JP | 11010771 | 1/1999 |
| WO | 8807214 | 9/1988 |
| WO | 9323251 | 11/1993 |
| WO | 9517475 | 1/1995 |
| WO | 9513569 | 5/1995 |
| WO | 9719820 | 6/1997 |
| WO | 9812583 | 3/1998 |
| WO | 0008596 | 2/2000 |
| WO | 0103945 | 1/2001 |
| WO | 0153113 | 7/2001 |
| WO | 0200446 | 1/2002 |
| WO | 0204234 | 1/2002 |
| WO | 0240599 | 5/2002 |
| WO | 0240600 | 5/2002 |
| WO | 02053677 | 7/2002 |
| WO | 02090002 | 11/2002 |
| WO | 03102084 | 12/2003 |
| WO | 2004/024836 | 3/2004 |
| WO | WO 2005/017048 | 2/2005 |

OTHER PUBLICATIONS

Llewellyn, "Dovids: Functional Beauty—discussion about holography", Paper, Film, and Foil Converter, Aug. 2002.
Hardin, "Optical tricks designed to foil counterfeiters", OE Reports, No. 191, Nov. 1999.
Argoitia and Witzman, Pigments Exhibiting Diffractive Effects, Soc. Of Vac. Coasters, 45$^{th}$ Annual Tech. Conf. Proceed. (2002).
Powell et al. (ED), "Vapor Disposition", John Wiley & Sons, p. 132, 1996.
Van Renesse (Ed.), "Optical Document Security", 2$^{nd}$ Ed., Artech House 254, 349-69 (1997).
Lotz et al., *Optical Layers on Large Area Plastic Films*, Precision, Applied Films (Nov. 2001).
Himpsel et al., *Nanowires by Step Decoration*, Mat. Research Soc. Bul., pp. 20-24 (Aug. 1999).
Prokes and Wang (ED.), *Novel Methods of Nanoscale Wire Formation*, Mat. Research Soc. Bul., pp. 13-14 (Aug. 1999).
Dobrowolski et al., "Research on Thin Film Anticounterfeiting Coatings at the National Research Council of Canada", Applied Optics, vol. 28, No. 14, pp. 2702-2717, Jul. 15, 1989.
Halliday et al, "Fundamentals of Physics, Sixth Edition", p. 662, Jul. 2000.
Argoitia et al, "Pigments Exhibiting Diffractive Effects", Soc. of Vac. Coaters, 45$^{th}$ Annual Tech. Conf. Proceed. (2002).
Argoitia et al, "The concept of printable holograms through the alignment of diffractive pigments", SPIE Conference on Document Security, Jan. 2004.
Coombs et al, "Integration of contracting technologies into advanced optical security devices", SPIE Conference on Document Security, Jan. 2004.
"Optical Thin-Film Security Devices", J.A. Dobrowolski, Optical Security Document, Rudolf Van Renesse, Artech House, 1998, pp. 289-328.
"Paper Based Document Security—a Review" Rudolf L. van Renesse, European Conference on Security and Detection, Apr. 28-30, 1997, Conference Publication No. 437, p. 75-80.
Diffractive Microstructures for Security Applications: M. T. Gale, Paul Scherrer Institute, Zurich, IEEE Conference Publication London 1991, pp. 205-209, Sep. 16-18, 1991.
Definition of "directly" from Webster's Third New International Dictionary, 1993, p. 641.
John M. McKiernan et al; "Luminescence and Laser Action of Coumarin Dyes Doped in Silicate and Aluminosilicate Glasses Prepared by Sol-Gel Technique," Journal of Inorganic and Organometallic Polymers, vol. 1, No. 1, 1991, pp. 87-103.
Jeffrey I. Zink et al, "Optical Probes and Properties of Aluminosilicate Glasses Prepared by The Sol-Gel Method," Polym. Mater. Sci. Eng., pp. 204-208 (1989).
"Security Enhancement of Holograms with Interference Coatings" by Phillips et al. Optical Security and Counterfeit Deterrence Techniques III Proceedings of SPIE vol. 3973 p. 304-316 (2000).
Don W. Tomkins, Kurz Hastings, "Transparent Overlays for Security Printing and Plastic ID Cards" pp. 1-8, Nov. 1997.
The Mearl Corporation Brochure for "Mearl Iridescent Film" Peekskill, NY.
J.A. Dobrowolski et al, "Optical Interference Coatings for Inhibiting of Counterfeiting" Optica Acta, 1973, vol. 20, No. 12, 925-037.
The R.D. Mathis Company Manual for "Thin Film Evaporation Source Reference" Long Beach, CA.
Minolta Manual for "Precise Color Communication, Color Control From Feeling to Instrumentation" pp. 18, 20, 22-23, 46-49.
Frans Defilet, LGZ Landis & Gyr Zug Corporation, "Kinegrams 'Optical Variable Devices' (OVD's) for Banknotes, Security Documents and Plastic Cards" San Diego, Apr. 1-3, 1987.
S.P. McGrew, "Hologram Counterfeiting: Problems and Solutions" SPIE, vol. 1210 Optical Security and Anticounterfeiting Systems, 1990, pp. 66-76.
Rudolf L. van Renesse, "Security Design Of Valuable Documents And Products" SPIE, vol. 2659, Jun. 1996, pp. 10-20.
Steve McGrew, "Countermeasures Against Hologram Counterfeiting" Internet site www.iea.com/nli/publications/countermeasures.htm, Jan. 6, 2000.
Roger W. Phillips, "Optically Variable Films, Pigments, and Inks" SPIE vol. 1323 Optical Thin Films III: New Developments, 1990, pp. 98-109.
Roger W. Phillips et al. "Optical Coatings for Document Security" Applied Optics, vol. 35, No. 28, Oct. 1, 1996 pp. 5529-5534.
J. Rolfe "Optically Variable Devices for use on Bank Notes" SPIE, vol. 1210 Optical Security and Anticounterfeiting Systems, pp. 14-19, 1990.
OVD Kinegram Cor "OVD Kinegram Management of Light to Provide Security" Internet site www.kiknegram.com.xhome.html, Dec. 17, 1999.
I.M. Boswarva et al., "Roll Coater System for the Production of Optically Variable Devices (OVD's) for Security Applications" Proceedings, 33$^{rd}$ Annual technical Conference, Society of Vacuum Coaters, pp. 103-109 (1990).

\* cited by examiner

NON-TOXIC FLAKES FOR AUTHENTICATION OF PHARMACEUTICAL ARTICLES

CROSS-REFERENCE TO RELATED APPLICATIONS

The present application is a continuation-in-part of U.S. patent application Ser. No. 10/641,695 filed Aug. 14, 2003 now U.S. Pat. No. 7,258,915, entitled "Flake For Covert Security Applications", and claims priority from U.S. Provisional Patent Application Ser. No. 60/807,097 filed Jul. 12, 2006, entitled "Food Safe Encoded Microflakes For Pharmaceutical Or Nutriceutical Tablet Labeling" the disclosures of which is incorporated herein.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates generally to non-toxic inorganic flakes, and more particularly to their use for authentication of pharmaceutical, nutraceutical, or veterinarian articles.

BACKGROUND OF THE INVENTION

Specialty pigments have been developed for use in security applications, such as anti-counterfeiting devices printed on banknotes, packaging of high-value items, seals for containers, and even for direct application to commercial items. For example, the U.S. twenty-dollar Federal Reserve Note currently uses optically variable ink. The number "20" printed in the lower-right corner of the face of the note changes color as the viewing angle changes. This is an overt anti-counterfeiting device. The color-shifting effect is not reproducible by ordinary color photocopiers, and someone receiving a note can observe whether it has the color-shifting security feature to determine the note's authenticity.

Other high-value documents and objects use similar measures. For example, iridescent pigments or diffractive pigments are used in paints and inks that are applied directly to an article, such as a stock certificate, passport, original product packaging, or to seals that are applied to an article. Unfortunately, counterfeiters continue to become more sophisticated. Security features that are more difficult to counterfeit are desirable.

One anti-counterfeiting approach uses microscopic symbols on multi-layer color-shifting pigment flakes. The symbols are formed on at least one of the layers of the multi-layer color-shifting pigment flakes by a local change of an optical property(s), such as reflectivity. The multi-layer color-shifting pigment flakes generally include a Fabry Perot-type structure having an absorbing layer separated from a reflective layer by a spacer layer. The reflective layer is typically a layer of metal, which renders the pigment flake essentially opaque. If a large portion of these types of pigment flakes are mixed with other pigment, the resultant color might be significantly different from the pigment.

Clear pigment flakes with holographic information are also used for anti-counterfeiting purposes. A monochromatic volume hologram is formed in a polymeric platelet using a reference laser light in the visible, infrared ("IR"), or ultraviolet ("UV") region. The polymeric platelet does not have a metallic reflective layer, and may be mixed in with other coatings, including metallic coatings (e.g. inks and paints), without disturbing the subjective color appearance of the coating. The polymeric platelets can also be incorporated in a varnish coating, which may be applied over an article without changing its color. When the polymeric platelets are irradiated with the reference laser light, the hologram may be read for the information it contains. However, polymeric materials may break down in sunlight and holograms have become relatively easy to counterfeit because an original hologram can provide a "fingerprint" (template) that facilitates copying. Holograms are not as strong an anti-counterfeiting device as they used to be.

It is desirable to mark objects with covert anti-counterfeiting devices that overcome the limitations of the techniques discussed above.

BRIEF SUMMARY OF THE INVENTION

A coating composition includes covert flakes with identifying indicia made of a single layer of inorganic dielectric material. Examples of identifying indicia include selected flake shape(s) and/or symbol(s). The covert flakes are typically dispersed in a carrier, such as a varnish base, paint vehicle or ink vehicle, to form a coating composition. The covert flakes are dispersed in sufficiently dilute concentration so that the covert flakes are not easily detectable in the coating composition by casual observation and can be clear or colored to match the color of a base pigment.

In a particular embodiment, covert security flakes fluoresce when illuminated with non-visible radiation. In an embodiment of the invention, fluorescing covert security flakes make up less than 1% of the composition.

In another embodiment, clear covert flakes in a varnish composition make up to 20% of the composition. In another embodiment, clear covert flakes make up to 10 weight percent of a total pigment weight in a composition having optically variable base pigment flakes.

In a particular embodiment the covert flakes are a single layer of an inorganic dielectric material, such as ZnS. The thickness of the single layer of inorganic dielectric material is selected to provide a covert flake that has color, or that is clear. In a further embodiment, clear covert flake is heat-treated to improve its clarity (i.e. "whiteness").

In another embodiment, a coating composition has clear covert flakes that are not easily detectable in the coating composition by observation under visible light dispersed in a carrier. The clear covert pigment flakes fluoresce when illuminated with UV light and have one or more symbols readable under visible light at a magnification of 50.times.-200.times. In a particular embodiment, the clear covert flakes in the carrier have a transmittance of more than 70% in the visible region.

A composition according to an embodiment of the present invention is applied to an object to provide a covert security feature. A pigmented composition may be used to print a field (e.g. an image) on the object, and a varnish composition may be used to print a clear field on the object, or to overprint an existing image on the object. In an embodiment of the invention, covert flake is mixed with base pigment to provide a covert security feature to images printed with the composition that look substantially similar to images printed with the base pigment.

In a method according to an embodiment of the present invention, symbols on covert flakes are not readable when the covert security feature is illuminated with non-visible radiation, i.e. when the flake is fluorescing. The location of a covert flake is identified using non-visible radiation, and then the flake is observed under visible light (typically under magnification of 50.times.-200.times.) to read the symbol(s) on the covert flake.

In one embodiment of the present invention, non-toxic inorganic flakes are used for identification and anticounterfeit protection of pharmaceutical, nutraceutical, or veterinarian unit-dosage articles, such as pills, tablets and capsules, having a core essentially consisting of a biologically active material and/or a biologically inert material. Non-toxic inorganic authentication flakes, either optically variable flakes having at least one metallic layer or taggant flakes, are disposed within the core or on the surface of the article.

In another embodiment of the present invention, non-toxic inorganic authentication flakes are dispersed within a pharmaceutical, nutraceutical, or veterinarian ointment.

DETAILED DESCRIPTION OF THE INVENTION

Figure 1:
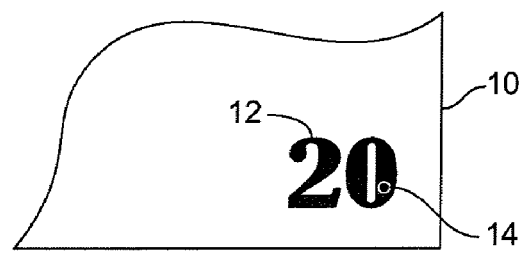
FIG. 1 is a plan view of a portion of a document with a security feature according to an embodiment of the present invention.

I. Introduction.

Flakes for covert security applications are not typically seen by casual observation. Some sort of inspection technique, such as inspection under a microscope or illumination with a particular type of light, is used to find and/or read the flakes. Flakes according to embodiments of the invention can be colored ("pigment flakes") or essentially clear.

In one embodiment, flakes containing indicia, such as a symbol or a particular shape, substantially match the visual characteristics of a bulk pigment or other substance they are mixed with. In a particular embodiment, a single-layer inorganic flake having a selected shape or symbol is mixed with an iridescent mica-based flake or other base pigment. In another embodiment, clear flakes having indicia are mixed with bulk pigment without disturbing the visual characteristic of the resultant mixture. In yet another embodiment, clear flakes having indicia are mixed in a varnish and applied over an object to provide a covert security feature without substantially changing the underlying color. As used herein, a varnish is generally a substantially clear composition.

In a particular embodiment, flakes made from a single-layer of ZnS are heat-treated to whiten or "bleach" the appearance of the flake and improving the clarity (i.e. reducing the yellow nature) of the resultant composition. For the purpose of this discussion, a "single layer" of inorganic material includes multiple layers of the same inorganic material built up upon each other.

In yet another embodiment, covert flakes are mixed with a chemical, such as an explosive, explosive precursor, food, drug, or controlled substance. The covert flakes include indicia, such as symbols and/or other patterning (e.g. grooves) and specific shapes that identify the manufacturer or provide other specific information. Inorganic flakes are particularly desirable in applications where heat, solvents, sunlight, or other factors may degrade organic flakes. For example, an inorganic covert flake used in an explosive is detectable even after exposure to high temperatures and/or pressures, and is persistent in the environment.

In a particular embodiment, authentication flakes including OV flakes and taggant flakes are used for labeling pills, tablets, suppositories, capsules, or ointments containing biologically active material. Alternatively, the biologically active material can be added or replaced by a biologically non-active material, for example for placebo trials.

Many materials conventionally used for optical flakes are not safe for ingestion. In particular, Zinc sulfide is an irritant when ingested due to the production of hydrogen sulfide. Some materials, like lead, arsenic, and cadmium, are poisonous or carcinogenic. Other materials can only be used in very trace amounts, for example, selenium, chromium or cobalt; heavy metals must be limited in their dosage. Aluminum is often referred as harmful material, however it is a component of certain antacids, and some baking powders contain sodium aluminum sulfate. Safety of a particular material depends on an amount ingested and should be evaluated separately for different patient groups.

For use in the pharmacology or food industry, the authentication flakes are made of non-toxic, preferably inert, materials. The term "non-toxic" is used here in its broadest sense meaning that the substance is not harmful and may be safely ingested. The non-toxic, or edible, authentication flakes are applied on the surface or within pills, tablets, suppositories, or capsules containing liquid, powdered, or granulated medicine. Alternatively, the authentication flakes are used in a pharmaceutical, nutraceutical, or veterinarian ointment as dispersed within an ointment base.

In accordance with the present invention, inorganic compounds like silica, titania, alumina, are used in non-toxic authentication flakes, since they are inert and safe to ingest, and they are persistent and detectable by their difference from the organic materials of the coating or tablet under a microscope.

Non-toxic dielectric materials include inert materials, such as $SiO_2$, and materials approved by the FDA as food additives and colorants, such as iron oxides and titanium oxides. Other materials, such as MgO and ZnO are actually nutrients and are acceptable in small quantities. MgO is used as an antacid, and has a Recommended Daily Allowance (RDA) of about 300 milligrams or more. ZnO is also a micronutrient and has an RDA of 10-15 milligrams.

Some of the dielectric materials are clear materials, including SiO2 and TiO2, MgO and ZnO. Other non-toxic dielectric materials, such as SiO, Iron oxides and some of the Ti oxides are absorbing depending on their degree of oxidation. Doped dielectric materials, such as Fe doped SiO2, Ti doped Al2O3, etc, are colored dielectric materials. In some embodiments, the flakes are thermally treated to achieve a desired coloration. Also, irradiation of dielectric materials is used in Jewelry industry to induce color. Such materials are used in single layered colored taggant flakes.

Non-toxic dielectric materials are used, in particular, for manufacturing single-layered taggant flakes, clear or colored, as described hereinbelow. Preferably, taggant flakes are single layered to reduce the amount of "foreign" material delivered to the organism; however, authentication flakes can consist of more than one layer. Flakes having an absorbing dielectric layer over a reflector layer exhibit a strong coloration, which is dependent on both thin film interference effects and the intrinsic coloration or absorbance of the material itself. Even a weakly absorbing dielectric layer together with a reflector layer provides a vivid effect vivid, with the quite bright reflectance.

Non-toxic authentication flakes require materials which are physiologically inert, like aluminum oxide, titanium dioxide, the silicon oxides, and iron oxides. Preferred metals for use in authentication flakes are well tolerated by the body and considered a part of a normal diet.

Metals such as titanium, gold, silver, zinc, magnesium, iron, or metal compounds such as carbides or nitrides, for example, TiN, TiC, TiOxCyNz, etc, are used in non-toxic flakes to improve visibility and add coloration, and add overt recognition without compromising edibility. Despite small particles of iron are easily absorbed, the total amount of iron in flakes on one pill is about a few micrograms, whereas over-the-counter vitamins typically contain 18 milligram of iron per pill. Chromium is also used as a food supplement in amounts above 100 microgram a day. Many metals are tolerated and even required by the body in small quantities. There are medical references to the body's need for trace metals, see for example http://www.merck.com/mmhe/sec12/ch155/ch155a.html#tb155_1. However, the toxicity of other materials is based on toxicological rather than nutritional studies. One way to access this information is through their Materials Safety Data Sheet (MSDS). The silver, gold, and copper, or bronze, sprinkles used on baked goods are called dragees. They have small amounts of the relevant metals as coatings but are considered non toxic by the FDA.

Advantageously, the non-toxic authentication flakes are very thin, hence the amount of "foreign", even though non-toxic, material introduced per pill would be very small, by way of example in milligram or even microgram quantities. Spot-printing of the flakes onto pills or capsules further reduces the amount of "foreign" material.

A quick calculation based on 20 micron square by 0.5 micron thick flakes of pure materials gives a total weight for 10,000 flakes of these materials of about 3-10 micrograms depending on exact composition and size of the flakes, so that less than 1%, even less than 0.1% in most cases, of the pill consists of the authentication flakes. This number of flakes per pill ensures that the flakes are easy to identify on the surface of the pill.

In one embodiment, the non-toxic flakes are dispersed in a non-toxic carrier, making a non-toxic composition for covering pills or forming capsules cases for a medicine. Alternatively, non-toxic composition is spot-printed onto pills or capsules thus reducing the amount of flake material. The non limiting examples of non-toxic carriers are gelatin, propylene glycol alginate (PGA), agar, carrageenan, alginic acid or salt thereof, gums, such as gum arabic, gellan gum, xanthan gum, and the like, and celluloses such as HPMC, HPC, HEC, CMEC, HPMCP, and the like, polyvinyl pyrrolidone, maltodextrin, polydextrose, modified starches. Other conventionally employed polymers and resins of this type may be employed.

As the authentication flakes are non-toxic and preferably inert, the amount of flakes in the coating is determined by either FDA regulation which governs the quantity of non-active material fillers or the desire for the flakes to be non-obvious or covert. The concentration by weight is dependent on whether the taggants are spot printed, and whether only the tablet coating or the entire dose weight is considered. Typically, the weight of authentication flakes is less than 10% of the coating weight, preferably, less than 1%, and, more preferably, less than 0.1%.

Alternatively, non-toxic flakes can be pressed into the surface of non-coated pills or tablets.

In one embodiment of the present invention, the authentication flakes are dispersed within the core of a pill or tablet or capsule, essentially consisting of a biologically active or inert material, or a mixture thereof. In this context, "essentially" means that authentication flakes can be added to the material of the core, amounting to no more than 5% of the weight. Preferably, no more than 1% of the article consists of the authentication flakes. However, it might be more if non-toxic flakes are used for labeling very small particles, by way of example, an individual particle in a "timed release" formulation. When the taggants are used forensically, as part of the body of the pill, they are dispersed through the volume of the pill or tablet or capsule. More flakes are needed so that they can be readily located. To detect those particles, the pill is typically dissolved and the residue examined for the taggants.

In one embodiment of the present invention, the authentication flakes are non-toxic inorganic taggant flakes, preferably single-layered. Taggant flakes, also referred to as taggent flakes, are encoded with information, either in the form of a grating and/or one or more symbols on the surface of the flake, or in the form of a selected shape. Multiple distinguishing effects are possible on a flake, for example, it can be a shaped flake with a one or two dimensional grating and a superimposed symbol. The features work in combination to form a unique taggant. The material too is a feature which can be subjected to analysis albeit forensic.

In particular, taggant flakes having grating thereon are disclosed in U.S. Pat. No. 6,815,065 in the names of Argoitia et al.; the taggant flakes having symbols thereon, and frames or borders embossed, etched or lasered into the flake for protecting the symbols during the process of separating flakes from their temporary support backing are disclosed in U.S. Patent Application No. 20060035080 by Argoitia; both documents are incorporated herein by reference.

In one embodiment of the present invention, the authentication flakes are single layered metal taggant flakes, made of non-toxic material, gold by way of example. Taggant flakes are described in more detail hereinbelow.

Alternatively, the authentication flakes are non-toxic optically variable flakes, in particular including a Fabry-Perot interference structure consisting of a reflector layer, a dielectric layer, and an absorber layer. Conventional OV flakes made with Al, $MgF_2$ and Cr, are not recommended for ingestion, since Al and $MgF_2$ are not desirable, and only Chromium may only be considered safe in extremely small amounts. Care should be taken to use only non-toxic materials. By way of example, an iron, zinc, magnesium, titanium, gold, silver or iron reflector and an inert or food safe dielectric, such as aluminum oxide, titanium oxide, or a silicon oxide, can be used in non-toxic OV flakes. For the absorber layer, chromium can be used in appropriately small amounts, or another, better tolerated or physiologically acceptable aforementioned metal.

Alternatively, multilayered OV flakes are all-dielectric, for example, having alternating layers of high- and low-index materials such as disclosed in the U.S. Pat. No. 6,815,065 to Argoitia, et al. For example, non-toxic OV flakes are made of $SiO2/TiO2$ multilayers.

The authentication OV flakes can have a particular or random shape, in the latter case the color shifting effect is used for authentication purposes. The OV flakes having a particular shape or symbol or grating, are referred to as OV taggants.

Advantageously, individual pills can be marked with taggants using conventional printing or coating methods, so that special application equipment is not required. Further, the pharmaceutical manufacturers may carry a stock of variously encoded taggants and apply them singularly or in various changeable combinations at their own discretion, maintaining the coding information within their own organization and varying it according to their needs. By varying the location of taggants on the pill, and the combination of taggants code used, each lot may be customized with unique information.

Taggants having a particular shape or with surface relief indicia or both can be produced by sputtering or evaporation onto a pre-embossed surface, either a film carrier as currently used or a wax layer as described in the U.S. Pat. No. 6,376,018 in the name of a co-inventor of the present invention. It is likely that dedicated machinery would be required for production to maintain material purity. In the case of deposition on a wax layer, a food grade paraffin may be used which could be incorporated directly into the tablet coating process.

Particular types of authentication flakes are described hereinbelow.

II. Exemplary Covert Flake

FIG. 1 is a plan view of a portion of a document 10 with a security feature 12 according to an embodiment of the present invention. At least a portion 14 of the security feature 12 is printed with ink or paint including clear or colored flakes having indicia (hereinafter "covert flakes") mixed with bulk pigment, such as bulk pigment flakes. In one embodiment, the covert flakes have a particular shape, such as being square, rectangular, trapezoidal, "diamond" shaped, or round, for example. In another embodiment, the covert flakes include a symbol and/or grating pattern, with or without having a selected shape. Covert flakes are also sometimes referred to as "taggent" flakes, although not all taggent flakes are necessarily covert flakes.

Generally, the bulk pigment particles have an irregular shape. In one embodiment, the covert flakes are distinguishable from bulk pigment particles, including bulk pigment flakes, by their shape. Alternatively, bulk pigment flakes have a first selected shape, and the covert flakes have a second selected shape. Production of shaped pigment flakes is accomplished by a variety of techniques, such as using a patterned substrate to deposit the flake material on the substrate and then separating the flake from the substrate to obtain the pattern, or using a laser or other means to cut the patterned flakes from a sheet of flake material. The selected shape of the covert flakes may be associated with a manufacturing facility, date of manufacture, or other aspect of the document 10, or ink used in producing the document, for example.

A roll coater is one type of apparatus that can be used to produce covert flakes according to embodiments of the invention. A roll of a sheet of polymer substrate material (also known as a "web") is passed through a deposition zone(s) and coated with one or more thin film layers. Multiple passes of the roll of polymer substrate back and forth through the deposition zone(s) may be made. The thin film layer(s) is then separated from the polymer substrate and processed into flake. Other apparatus and techniques may be used.

Alternatively or in addition to having a selected shape, the covert flakes may include one or more symbols. The symbol could be a letter, number, or other marking. A symbol could indicate the manufacturer of the covert flake, the user of the covert flake, or a date code, for example. The symbol(s) could be embossed on a substrate used in a roll coater prior to depositing thin film layers that are processed into flakes, or formed on the thin film layers after deposition, such as by laser ablation, embossing, or etching, for example.

A pigment flake with a selected shape or symbol provides a security feature even if it is easily observable; however, if a pigment flake with a selected shape or symbol is not easily observable, a counterfeiter might not even be aware that a covert flake is present. One embodiment of the present invention uses covert pigment flake that has the same optical characteristics as the base pigment. The percentage of covert pigment flakes is sufficiently small so that the covert pigment flakes are not easily found, even under microscopic examination. For example, if an ink composition has covert pigment flakes making up less than 1% of the total weight of pigment (i.e. base pigment plus covert pigment), the covert pigment flakes are difficult to find.

Another approach is to use a clear, inorganic covert flake with a selected shape or symbol. In one embodiment, clear inorganic covert flakes are mixed with base pigment flakes in a carrier, such as an ink vehicle or a paint vehicle, to form a composition, such as ink or paint. In another embodiment, the clear inorganic covert flakes are mixed in a clear carrier to form a varnish. The index of refraction of the carrier is sufficiently similar to the index of refraction of the clear covert flake so that the covert flake "disappears" in the carrier. Examples of carriers include polyvinyl alcohol, polyvinyl acetate polyvinylpyrrolidone, poly(ethoxyethylene), poly (methoxyethylene), poly(acrylic) acid, poly(acrylamide), poly(oxyethylene), poly(maleic anhydride), hydroxyethyl cellulose, cellulose acetate, poly(sacchrides) such as gum arabic and pectin, poly(acetals), such as polyvinylbutyral, poly(vinyl halides), such as polyvinyl chloride and polyvinylene chloride, poly(dienes) such as polybutadiene, poly (alkenes) such as polyethylene, poly(acrylates) such as polymethyl acrylate, poly(methacrylates) such as poly methylmethacrylate, poly(carbonates) such as poly(oxycarbonyl oxyhexamethylene, poly(esters) such as polyethylene terephthalate, poly(urethanes), poly(siloxanes), poly (suphides), poly(sulphones), poly(vinylnitriles), poly(acrylonitriles), poly(styrene), poly(phenylenes) such as poly(2,5 dihydroxy-1,4-phenyleneethylene), poly(amides), natural rubbers, formaldehyde resins and other polymers.

The clear covert flake does not typically become totally invisible in the carrier, but becomes less visible than it is in air.

If an observer knows where to look, the clear flake typically has a shadowy appearance, as do symbols formed in or on the clear flake. However, if one does not know where or how to look for the clear flake, it usually goes undetected.

In a particular embodiment, the clear covert flake has a reflectivity in the visible range of about 30% in air, and less than 30% reflectivity in the carrier. Thus, the clear covert flake typically has a transmittance of more than 70% when dispersed in the carrier, which maintains the visible characteristics of the base pigment that the clear covert flake is mixed with or that underlies a varnish containing the clear covert flake.

Clear, inorganic covert flakes are difficult to detect, even when they make up more than 1% of the total pigment weight in a composition or varnish. In one embodiment, the clear covert flake is a single layer of ZnS heat-treated to fluoresce under UV light. The location of the ZnS covert flake is illuminated with UV light to identify its location, and then it is observed using visible light, typically under a microscope at about 20.times.-200.times., to observe the indicia of the covert flake.

Figure 2A:
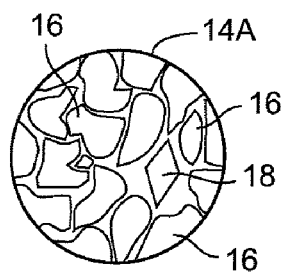
FIG. 2A is a simplified plan view of a portion of a security feature according to an embodiment of the present invention.

FIG. 2A is a simplified plan view of a portion 14A of a security feature according to an embodiment of the present invention. The portion 14A of the security feature is viewed under magnification, typically about 20.times.-200.times., in order to see the shape of the flakes, which are typically about 5-100 microns across, more typically about 20-40 microns across. The security feature has been printed with ink including base pigment particles 16 and a covert pigment flake 18 having a selected shape, in this case a "diamond" shape. The base pigment particles are illustrated as being irregularly shaped flakes. Alternatively, the base pigment particles are flakes having a selected shape. The covert pigment flake has similar optical characteristics as the base pigment particles, otherwise does not disturb the visual appearance of a composition made with the base pigment particles.

When the covert pigment flake is illuminated with non-visible radiation, such as UV or IR light or an electron beam, the covert pigment flake glows. In a particular embodiment, the covert pigment flake fluoresces under UV light. Illuminating the covert pigment flake with non-visible radiation allows an observer to identify where the covert pigment flake is located in the security feature, even if present in very small quantities. The observer then inspects the covert pigment flake under visible light to see the selected shape of the covert pigment flake, or to see the symbol(s) on the covert flake.

Figure 2B:
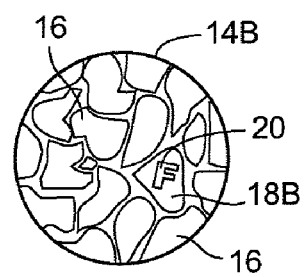
FIG. 2B is a simplified plan view of a portion of a security feature according to another embodiment of the present invention.

FIG. 2B is a simplified plan view of a portion of a security feature 14B according to another embodiment of the present invention. The security feature has been printed with ink including base pigment particles 16 and a covert pigment flake 18B having an irregular shape and containing a symbol 20, in this case a stylized "F". Several different symbols and combination of symbols could be used. The portion 14B of the security feature is viewed under magnification, typically about 100.times.-200.times., in order to see the symbol(s), which are typically about 0.5-20 microns high, on the covert pigment flake 18B.

The covert pigment flake 18B was made by depositing one or more thin film layers on a substrate, such as a plastic film, separating the thin film layer(s) from the substrate, and processing the separated thin film layer(s), such as by milling and sieving, into the desired flakes. The covert pigment flakes are typically about 5-100 microns across, and more typically about 20-100 microns across. The symbol 20 is typically about 0.5-20 microns tall. In a particular embodiment, the symbol 20 is about 700 nanometers tall and in another embodiment the symbol is about 15 microns tall. It is generally desirable to have the symbols sufficiently close so that most flakes have at least an identifiable portion of a symbol. In one embodiment, symbols that were 8 microns tall were spaced about 2 microns apart, which resulted in covert flakes having about 6 symbols per flake, on average. Symbols having bilateral symmetry appear the same whether viewed from the top or the bottom of a clear flake, but such symmetry is not required. In another embodiment, symbols that were about 15 microns tall were spaced about 4 microns apart.

The symbols are typically embossed on the substrate, and the thin film layer(s) deposited over the embossed substrate. The surface of the substrate, namely the symbol, is replicated in at least the first thin film layer that is deposited on the substrate, in either positive or negative relief. Thus, when the thin film layer(s) is separated from the embossed substrate and processed into flake, at least some of the flakes contain the symbol. The spacing of embossed symbols on the flake can be selected so that essentially every flake above a certain size will contain at least one symbol.

The base pigment particles are illustrated as being irregularly shaped flakes. Alternatively, the base pigment particles have a selected shape. Similarly, the covert pigment flake 18B could have a selected shape, in addition to the symbol 20, and a superimposed grating, such as a diffraction grating, could be included either over the entire flake or over selected portions of the flake, such as over the field of the flake, but not over the symbol. Alternatively, one type of grating is formed in the field of the flake, and another type of grating (e.g. with different pitch) is formed in the symbol area. The addition of a grating further increases the difficulty of counterfeiting. The covert pigment flake has generally the same optical characteristics as the base pigment particles, or is present in sufficiently small quantities so as not to disturb the visual appearance of a composition made with the base pigment particles.

In a particular embodiment, the base pigment particles are flakes of mica coated with a layer of $TiO_2$ or other dielectric material. The coating material typically has a relatively high index of refraction. Mica is a naturally occurring mineral that is relatively inexpensive and easily processed into flake substrate. When mica flake substrate is coated with a layer of high-index material of a selected thickness, a nacreous pigment flake is obtained. Mica flake substrate can be coated with several alternative materials using a variety of processes. Such pigments are commonly known as "mica-based" pigments. A photocopy of an image printed with such nacreous pigment flakes does not look like the original, thus mica-based pigment flakes are desirable for use to provide overt security features. However, shaping mica flake substrate or providing a symbol on mica flake substrate is impractical. Covert pigment flake according to an embodiment of the present invention is mixed with the mica-based pigment to enable a covert security feature to be included in images printed with mica-based pigment flakes. Covert pigment flakes made of a single layer of inorganic dielectric material, such as $TiO_2$ or ZnS, can have an appearance similar to a mica-based pigment if the covert pigment flake has a thickness about five times the quarter-wave optical thickness ("QWOT") at a selected wavelength in the visible spectrum. Typically, a single-layer covert pigment flake of ZnS or $TiO_2$ intended to match the appearance of a mica-based pigment has a thickness of about 60 nm to about 600 nm. In one embodiment of the present invention, non-toxic single layered taggant flakes made of inert $TiO_2$ having a predetermined shape and/or a symbol on the surface are used for authentication of pills, capsules with medicine, tablets, etc. For identification purposes, color centers are introduced into $TiO2$, or it can be sensitized with dyes to enhance electro-optical activity, most notably for photovoltaic applications. Such flakes can be identified by fluorescence or spectrometry.

Figure 2C:
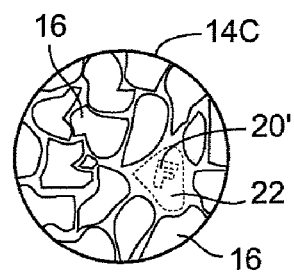
FIG. 2C is a simplified plan view of a portion of a security feature according to yet another embodiment of the present invention.

FIG. 2C is a simplified plan view of a portion of a security feature 14C according to yet another embodiment of the present invention. The security feature has been printed with ink including base pigment particles 16 and a clear covert flake 22 having an irregular shape and containing a symbol 20', in this case a stylized "F". Several different symbols and combination of symbols are alternatively used. Alternatively, a clear covert flake has a selected shape, with or without a symbol.

The clear covert flake is formed from a deposited (i.e. synthetic), inorganic thin film layer and in a particular embodiment is a single layer of ZnS about 700 nm thick. In a further embodiment, the ZnS flake it treated to enhance fluorescence. Alternatively, other materials that fluoresce visible light when exposed to UV light are used in other embodiments, such as zinc silicate, calcium-tungsten oxide, yttrium phosphate vanadium, doped yttrium oxide (such as with europium), and alkaline earth aluminates doped with rare earth aluminates, to name a few. Alternatively, other materials that fluoresce in the long UV range (300-400 nm) when excited with low UV radiation (about 250 nm) are used. Fluorescence is not required for all embodiments of the present invention.

In one embodiment, the material of the clear covert flake is chosen according to the intended carrier that it will be mixed with to obtain a selected match or mismatch of the index of refraction of the flake in the carrier. For example, when a clear flake made from a low-index material is mixed in a low-index carrier, the clear flake is very difficult to see. If the low-index clear flake is mixed in a high-index carrier, the clear flake is easier to see, but still not generally detected by casual observation.

Single layer flakes made of inorganic materials more than about ten QWOTs thick tend to be clear, rather than tinted or nacreous. However, even clear flakes can impart a yellowish tinge to a composition, such as a varnish. It was discovered that heat-treating some clear inorganic flakes improved their "whiteness", resulting in a superior varnish for use in covert security applications. In a particular embodiment, clear pigment flakes made from a single layer of ZnS about 700 nm thick were heated in air to a temperature of 550.degree. C. for about 600 minutes to enhance fluorescence under UV light. This heat treatment also improved the whiteness of the ZnS flake.

It is thought that trace elements remaining from the roll-coating process contributed to the enhanced fluorescence. In particular, NaCl was used as a release layer on the polymer substrate used in the roll coating process. A single layer of ZnS was deposited over the NaCl release layer, which was subsequently dissolved in water to facilitate removal of the ZnS from the polymer substrate. It is thought that sodium from the release layer doped the ZnS or activated other dopants, resulting in enhanced fluorescence.

Figure 3:
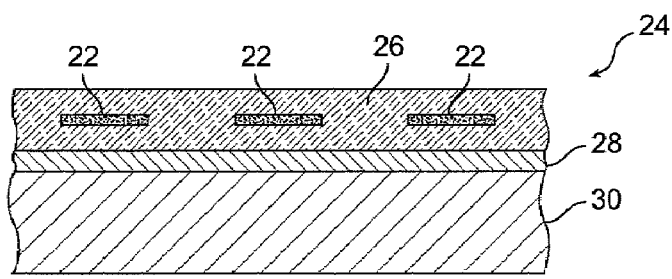
FIG. 3 is a cross section of a varnish with clear covert flakes dispersed in a carrier according to an embodiment of the present invention.

FIG. 3 is a cross section of a varnish 24 with clear covert flakes 22 dispersed in a carrier 26 according to an embodiment of the present invention. An optional color coat 28 has been applied to an object 30 underneath the varnish 24. The varnish 24 provides a covert security feature to the object without disturbing its appearance. In a particular embodiment, the optional color coat 28 is an image printed with nacreous or color-shifting pigment to provide an overt security feature to the object. The object is a document, product, packaging, or seal, for example. The varnish 24 enables providing a covert security feature to an object that already has a covert security feature without significantly altering the appearance of the object. For example, if stock certificates have been printed with overt security features and it subsequently becomes desirable to provide a covert security feature to the stock certificates, the overt security feature is overprinted with the varnish or a similar clear ink composition. In another embodiment, an additional covert security feature is provided to an object already having one or more covert security features. In a particular embodiment, the clear covert flakes make up not more than 2% of the varnish. Additional discussion regarding varnishes is provided below in the section on experimental results. Alternatively, the varnish 24 is a non-toxic carrier for coating pills or tablets 30, and clear covert flakes 22 are made of $TiO_2$.

Figure 4:
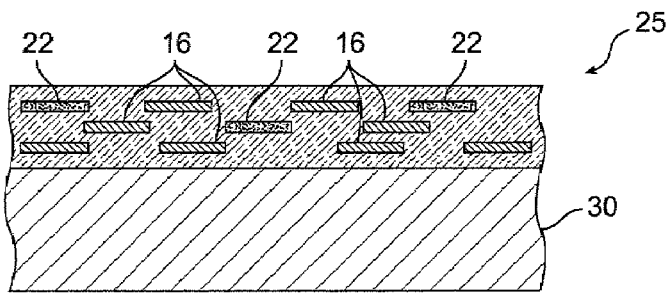
FIG. 4 is a cross section of base flakes and covert flakes dispersed in a binder according to another embodiment of the present invention.

FIG. 4 is a cross section of a composition 25 (e.g. ink or paint) including base pigment flakes 16 and clear covert flakes 22 dispersed in a binder according to another embodiment of the present invention. The clear covert flakes 22 have a symbol (see FIG. 2C, ref. num. 20'). Alternatively, the composition 25 includes selectively shaped clear flake, with or without a symbol(s), and/or covert pigment flake that is shaped and/or includes a symbol (see FIG. 2A, ref. num. 18 and FIG. 2B, ref. nums. 18B, 20). In one embodiment, the amount of clear covert flake 22 in the composition is less than 1% of the total weight of the base pigment flake 16 and clear covert flake 22 ("total pigment weight"), which sufficiently disperses the clear covert flakes in the base pigment flake to make casual detection of the covert flake difficult. In an alternative embodiment, the amount of clear covert flake in the composition is greater than 1%.

Adding covert flake to an existing ink or paint composition provides a covert security feature to images made of the ink or paint. For example, ink with color-shifting pigment is used to provide a color-shifting image as an overt security feature on a bank note or other object. Covert flake according to an embodiment of the present invention is added to the ink, and the resultant mixture is used to print images that appear substantially similar as those printed with the ink. Thus, a casual observer of the bank note does not notice a change in the appearance of the overt security feature (i.e. color-shifting image) after the covert security feature is added. The indicia of the covert flake indicates a date-of-manufacture, a printing location, and/or the source (manufacturer) of the ink, for example.

III. Identification of Covert Flakes

Figure 5A:
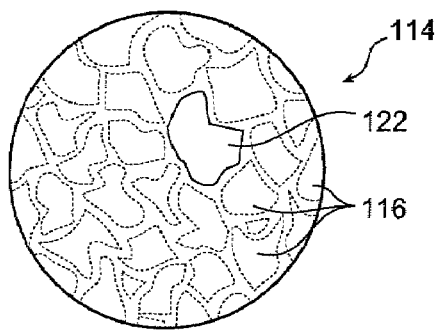
FIG. 5A is a simplified plan view of a portion of a security feature printed with clear, inorganic covert flake according to an embodiment of the present invention as seen under a microscope using UV illumination.

FIG. 5A is a simplified plan view of a portion of a security feature 114 printed with clear, inorganic covert flake 122 according to an embodiment of the present invention as seen under a microscope using UV illumination. The flakes are shown in a single layer for simplicity of illustration (compare FIG. 4). The clear covert flake 122 fluoresces (appears bright) and is easily distinguished from the base pigment flake 116, which appear dark and are shown in dashed lines for purposes of illustration. Typically, a much larger field of view is observed (i.e. lower magnification, typically 20.times.-50.times.). A reduced field of view is being shown for simplicity of illustration. Once the location of the fluorescent covert flake is identified, the viewer can "zoom-in" on the covert flake.

Figure 5B:
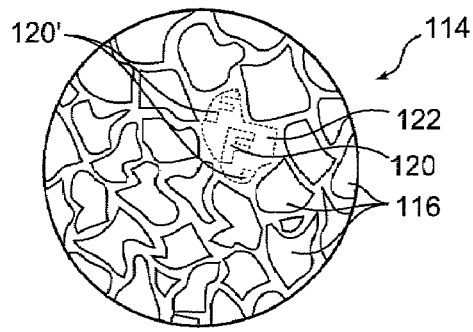
FIG. 5B is a simplified plan view of the portion of the security feature of FIG. 5A as seen under a microscope using visible light for illumination.

FIG. 5B is a simplified plan view of the portion of the security feature 114 of FIG. 5A as seen under a microscope using visible light for illumination. It was discovered that symbols on the clear covert flake were not easy to read under UV light because the fluorescence was a bulk phenomenon and obscured the symbol. When the UV light was switched off and the clear covert flake 122 was observed under a microscope using visible light, the faint outline of a symbol 120 (as well as the flake) was observable. Fluorescent covert flakes are particularly desirable when the concentration of flakes is low. The clear covert flake 122 and the symbol 120 are shown as dashed lines in this view to represent that they appear as faint outlines under visible light. The base pigment flakes 116 are shown as solid lines because they are typically prominent under visible light. In a particular embodiment, the clear covert flake was ZnS having an index of refraction of about 2.2 in a high-gloss varnish that was first observed under UV light, and then the symbol on the flake was read using visible light at a magnification of 100.times.

A similar result is expected for covert pigment flakes that fluoresce under UV light or other non-visible radiation. For example, covert pigment flake dispersed in base pigment flake having similar visual characteristics is difficult to detect when the covert pigment flake is sufficiently dilute. In one embodiment, the covert pigment flake has a selected shape that is observable under UV light. In another embodiment, the covert pigment flake has a symbol that is not easily observable under UV light, but is observable under visible light. The location of the covert pigment flake with the symbol is identified using UV light and then the UV light is switched off and the symbol is read using visible light.

Alternatively, a material that fluoresces at a shorter wavelength when illuminated with light at a longer wavelength is used to fabricate covert flakes or covert pigment flakes. It is believed that this type of fluorescence would be less easily noticed by a counterfeiter, enhancing it use in covert security applications. In one embodiment, near infrared or infrared light is used to illuminate covert flake or covert pigment flake to fluoresce in the visible range.

IV. Experimental Results

Prior to developing clear covert flake or single-layer covert pigment, various alternatives were evaluated. A test standard using 100% magenta-to-green optically variable intaglio ("OVI") pigment flake was produced and measured. All taggent samples had a grating pattern of 2000 lines/mm, which makes the taggent flakes easier to distinguish from the base flake (i.e. locate) and more difficult to counterfeit. The grating pattern did not induce diffractive properties to images printed with the test compositions. It is believed that the low portion of the taggent flakes in combination with not being well oriented to the viewer avoided a diffractive property from occurring. In a particular embodiment of the present invention, a grating pattern was included on taggent flakes with symbols. The symbols were identifiable under a microscope at a first magnification, but the grating pattern was not easily seen at this first magnification. The grating pattern was seen at a higher magnification. It is believed that including such a grating pattern further enhances the covert nature of the taggent flake because a counterfeiter might see the symbol under microscopic examination, but not see the grating pattern, and hence not include it in a counterfeit article.

The first test sample ("sample 1") contained 90% (by weight) of the conventional magenta-to-green pigment flake mixed with 10% magenta-to-green OVI pigment flake including symbols ("taggent flake"). The taggent flakes were easy to detect by routine microscopic inspection, and the color performance of the mixture was the same as the test standard because the color of the taggent flake was well matched to the color of the base flake. However, close color matching involves careful monitoring of the production of the taggent flake. Similarly, a new optical design for each color of taggent flake would generally be used to match each color of base flake. Thus, this approach does not provide a generic taggent flake that can be mixed with a variety of colored base pigments.

A simpler approach is to use a standard taggent flake design that can be used with many different colors of base flake. Single-layer MgF.sub.2 taggent flake (was mixed with the magenta-to-green OVI base pigment, the taggent flake making up 10% of the total pigment weight ("sample 2"). As with the color-matched OVI, color performance was essentially identical to samples produced with 100% base OVI pigment flake. However, the MgF.sub.2 flakes were difficult to detect under routine microscopic examination, even at a concentration of 10%.

"Silver" (aluminum) taggent flake was also evaluated. Fabrication of silver flake is relatively simple and these flakes were very easy to detect at a concentration of 5%. It was hoped that silver taggent flakes would be able to be mixed with many colors of base pigment. However, the color performance of an intaglio blend containing only 5% silver taggent flake mixed with the magenta-to-green OVI base pigment ("sample 3") was poor. Thus, silver taggent flake may be useful in certain compositions, but appear to degrade the color performance of at least some base pigments.

Finally, clear taggent flake was made from a single layer of ZnS. Production of this flake is relatively easy, and detectability at 10% concentration was easy, which is to say it was more difficult than detecting the OVI taggent flakes, but much, much easier than detecting the MgF.sub.2 taggent flakes. An intaglio blend with 10% ZnS flake and 90% magenta-to-green OVI flake ("sample 4") was compared against the test standard. The color performance was nearly equal, with a slight (about 3%) decrease in chroma. The persons involved in this subjective comparison are quite experienced in evaluating color performance of optically variable pigments, and used a side-by-side comparison against a standard. It is believed that 10% of this flake added to an existing ink or paint composition would preserve the color performance sufficiently so that an average observer would not notice any change. The ZnS clear taggent flake appears able to be added to a large number of colored pigments, including optically variable pigments without noticeably altering the appearance of compositions made with the colored pigments, and hence enables a generic taggent flake.

The measured optical performance of the samples described above is provided in Table 1:

TABLE 1

| Optical Performance of Intaglio Blends | | | | | |
|---|---|---|---|---|---|
| Sample # | L* | a* | b* | C* | h |
| Test standard | 49.27 | 40.32 | −31.05 | 50.89 | 322.4 |
| Sample 1 | 49.08 | 40.25 | −30.87 | 50.73 | 322.51 |
| Sample 2 | 49.42 | 40.62 | −31.04 | 51.12 | 322.61 |
| Sample 3 | 52.67 | 35.26 | −27.26 | 44.57 | 322.29 |
| Sample 4 | 49.66 | 39.22 | −29.85 | 49.29 | 322.72 |

Clear ZnS flake for use as a taggent or covert taggent was also evaluated in varnish compositions. It was determined that in some instances almost one-third of the varnish composition could be clear flake with almost no change in the perceived appearance of the varnish composition. A high-gloss varnish base was used to make the varnish compositions and the varnish compositions were applied to white card stock of the type normally used for color evaluation of inks and paints. All varnish compositions were compared against a test standard of the varnish base without clear flake.

In the first varnish composition, 3% of as-deposited (i.e. not heat-treated for clarity) single-layer ZnS looked essentially identical to the test standard. A second varnish composition having 5% single-layer as-deposited ZnS flake was barely noticeably different when compared against the test standard, but it is believed that a casual observer would not notice the slight amount of yellowing. A third varnish sample with 10% single-layer as-deposited ZnS flake exhibited a noticeable change in appearance when compared against the test standard, and it is believed that some casual observers would notice a field printed with this composition on a very light background. However, this composition might be useful for printing on non-white substrates, such as bank notes or off-white stock certificates, where the slight yellowing would be less likely to be noticed. Alternatively, a non-gloss varnish base is used to further reduce likelihood of detection when used as a covert security feature. A fourth varnish sample with 15% single-layer as-deposited ZnS exhibited noticeable yellowing, even without a side-by-side comparison with the test standard.

Single-layer ZnS flake was heat treated to clarify ("bleach") the flake. The flake was heated to 200.degree. C. for two hours in air. Heat treating ZnS flake to enhance fluorescence (550.degree. C. for 10 hours in air) also bleaches the flake, but bleaching can be achieved with the shorter heat treat. A varnish composition using 20% single-layer bleached ZnS showed almost no perceptible color change. Thus, it is believed that at least 10% of unbleached single-layer ZnS flake and at least 20% of bleached single-layer ZnS flake could be added to a high-gloss varnish base as a covert taggent.

ZnS is further desirable as a taggent flake because, unlike some flake including a metal (e.g. aluminum) layer, ZnS is durable in the presence of water, acid, base, and bleach. Unlike some organic flake, ZnS is also durable in the presence of organic solvents and sunlight.

Figure 6:
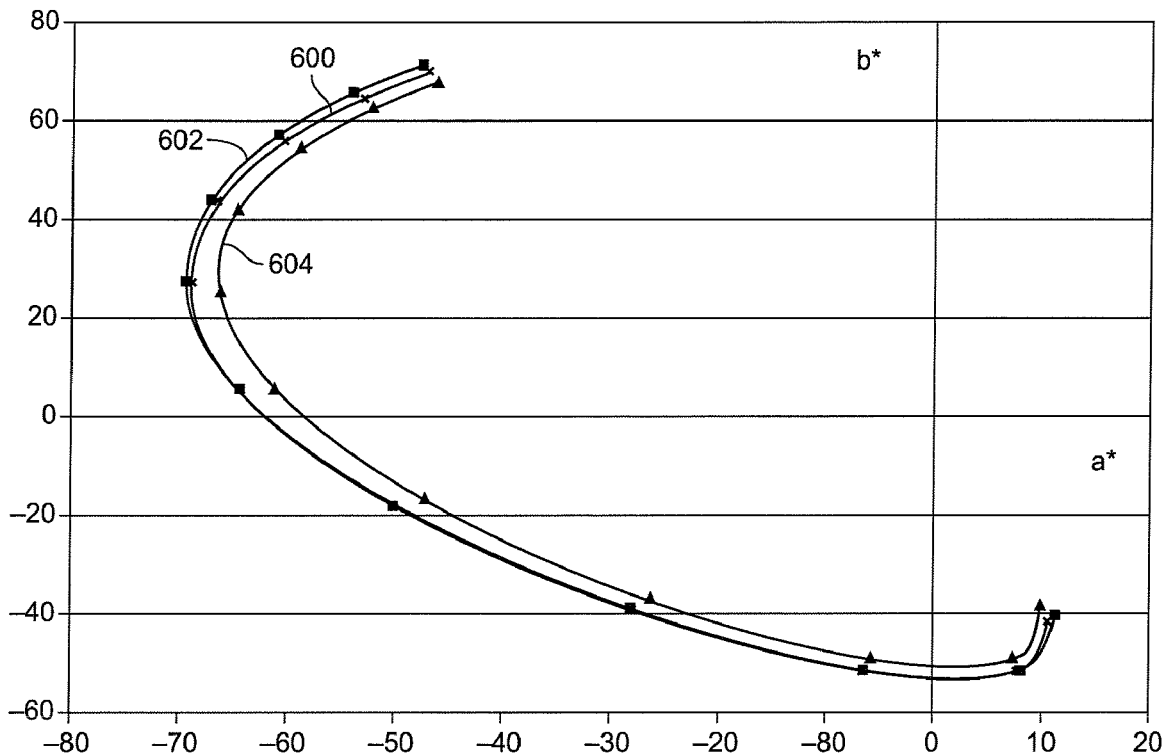
FIG. 6 shows the color travel for a test sample prepared with an ink, and for test samples prepared with the ink in combination with covert pigment flakes according to an embodiment of the present invention.

FIG. 6 shows the color travel for a test sample prepared with an ink, and for test samples prepared with the ink in combination with covert pigment flakes according to an embodiment of the present invention. The color plots are according to the CIE La*b* conventions. The illumination and viewing angles were ten degrees off from the specular angle to avoid the strong gloss component associated with clear-coated samples. The samples were characterized using eleven angles of illumination/viewing from 15.degree./5.degree. to 65.degree./55.degree. in 5.degree. increments. The first point of the curve (i.e. the upper left point) corresponds to the 15.degree./5.degree. datum, and the last (i.e. eleventh) point corresponds to the 65.degree./55.degree. datum.

A first curve 600 shows the measured color travel for a test sample prepared with blue-to-green optically variable pigment flake. A second curve 602 shows the measured color travel for a sample prepared with 95 weight percent blue-to-green optically variable pigment flake and 5 weight percent of single-layer ZnS flake about 700 nm thick and having an average particle size of about 20 microns. Symbols on the flake were about 8.times.6 microns, separated by about 2 microns of field. The weight percent is the percent of the total weight of the flake used to prepare the ink composition for the sample. A third curve 604 shows the measured color travel for a sample prepared with 90 weight percent blue-green optically variable pigment flake and 10 weight percent of the same ZnS flake used in the sample associated with the second curve. These curves illustrate that very similar optical performance is achievable for ink compositions having up to 10 weight percent covert flake. In particular, the color travel is nearly identical for all three samples, and the chroma is only slightly less for the sample made with 10% clear covert flake. Thus, a covert flake according to an embodiment of the present invention is added to an existing optically variable ink to form a composition to provide a covert security feature without significantly altering the appearance of images printed with the composition.

V. Exemplary Methods

Figure 7:
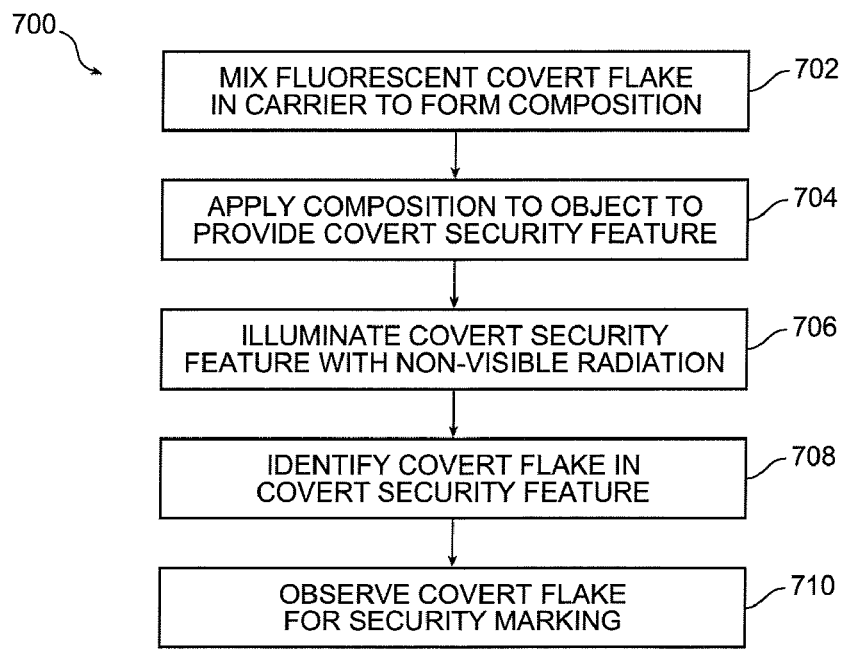
FIG. 7 is a simplified flow chart of a method of observing covert flakes according to an embodiment of the present invention.

FIG. 7 is a simplified flow chart of a method 700 of providing an object with covert flakes according to an embodiment of the present invention. Covert flakes that fluoresce under non-visible radiation are mixed in a carrier (step 702) to provide a composition, such as ink or paint, in which the covert flakes are not easily detectable by observation under visible light. In one embodiment, the covert flakes are clear covert flakes that have a symbol and/or a selected shape. In a further embodiment, the composition includes base pigment flakes or particles. In another embodiment, the covert flakes are covert pigment flakes that have a symbol and/or a selected shape. The composition is applied to the object (step 704) to provide a covert security feature. In one embodiment, the composition is applied using a printing step, such as a gravure, flexographic, offset, letterpress, intaglio, or screen printing step. In another embodiment, the composition is applied using a painting step, such as a rolling, dipping, brushing, or spray painting step.

After providing the covert security feature, the covert security feature is observed by illuminating the object with non-visible radiation (step 706) to cause the covert flakes to fluoresce and a covert flake is identified (step 708). If the composition has base pigment flakes or particles that also fluoresce, it is understood that the covert flakes fluoresce significantly more or less, or at a different color, than the base pigment flakes or particles so that the covert flakes stand out in the composition and are easily identified. The identified covert flake is observed (step 710) for a security marking. In one embodiment, the covert flake has a selected shape and is observed while the object is illuminated with non-visible radiation. In another embodiment, the covert flake includes a symbol, and the covert flake is observed using visible light after the step of identifying the covert flake using non-visible radiation. In a particular embodiment, the step of observing one or more symbols on the covert flake is done under magnification of 50.times.-200.times. While the invention has been described above in terms of various specific embodiments, the invention may be embodied in other specific forms without departing from the spirit of the invention. Thus, the embodiments described above illustrate the invention, but are not restrictive of the invention, which is indicated by the following claims. All modifications and equivalents that come within the meaning and range of the claims are included within their scope.

What we claim is:

1. A pharmaceutical, nutraceutical, or veterinarian unit-dosage article having a surface, comprising: a material selected from the group consisting of a biologically active material and a biologically inert material, and a mixture thereof; and authentication flakes selected from the group consisting of non-toxic, inorganic optically variable flakes having at least one metallic layer and non-toxic, inorganic taggant flakes; wherein the authentication flakes are dispersed within the article or on the surface.

2. An article defined in claim 1, wherein the material forms a core of the article; wherein the article further comprises a coating on at least a portion of the core, and wherein the authentication flakes are dispersed within the coating.

3. An article defined in claim 2, wherein the core is selected from the group consisting of a liquid, a powder, and granules, and wherein the coating forms a capsule case around the core.

4. An article defined in claim 2, wherein the authentication flakes form less than 10% by weight of the coating.

5. An article defined in claim 1, wherein the authentication flakes are non-toxic, inorganic taggant flakes having a predetermined shape.

6. An article defined in claim 1, wherein the authentication flakes are non-toxic, inorganic taggant flakes having indicia or a grating pattern thereon.

7. An article defined in claim 1, wherein the authentication flakes are non-toxic, inorganic taggant flakes having one or more frame borders along an edge thereof.

8. An article defined in claim 1, wherein the authentication flakes are non-toxic, single-layer dielectric taggant flakes.

9. An article defined in claim 1, wherein the authentication flakes are clear or colored taggant flakes.

10. An article defined in claim 1, wherein the authentication flakes are non-toxic, dielectric covert taggant flakes.

11. An article defined in claim 1, wherein the authentication flakes are non-toxic taggant flakes comprising a material selected from the group consisting of zinc, magnesium, iron, titanium, gold, and silver.

12. An article defined in claim 1, wherein the authentication flakes are optically variable non-toxic flakes, each comprising a non-toxic reflector layer, a non-toxic absorber layer, and a non-toxic dielectric layer therebetween.

13. An article defined in claim 12, wherein the non-toxic absorber layer comprises a material selected from the group consisting of iron, zinc, magnesium, iron, titanium, gold, and silver.

14. An article defined in claim 12, wherein the non-toxic reflector layer comprises a material selected from the group consisting of zinc, magnesium, iron, titanium, gold, and silver.

15. An article defined in claim 1, wherein the authentication flakes include a material selected from the group consisting of: $TiO_2$, TiO, SiO, $SiO_2$, ZnO, MgO, and oxides of iron.

16. An article defined in claim 1, wherein the authentication flakes are dispersed within the article and wherein the authentication flakes form less than 5% by weight of the article.

17. An article defined in claim 16, wherein the authentication flakes are dispersed within the article and wherein the authentication flakes form less than 1% by weight of the article.

18. A pharmaceutical, nutraceutical, or veterinarian ointment comprising: an ointment base selected from the group consisting of a biologically active material and a biologically inert material, and a mixture thereof; and authentication flakes selected from the group consisting of non-toxic, inorganic optically variable flakes and non-toxic, inorganic taggant flakes; and wherein the authentication flakes are dispersed within the ointment base.

19. An article defined in claim 18, wherein the authentication flakes form less than 5% of the ointment by weight.

20. An article defined in claim 18, wherein the authentication flakes are one selected from the group of taggant flakes having a predetermined shape, taggant flakes having one or more frame borders along an edge thereof, taggant flakes having indicia or a grating pattern thereon, single-layered clear dielectric taggant flakes, and single-layered colored taggant flakes.

* * * * *